United States Patent
Banerjee et al.

(10) Patent No.: US 10,776,621 B2
(45) Date of Patent: Sep. 15, 2020

(54) SYSTEM AND METHOD FOR SIGNAL ANALYSIS

(71) Applicant: Tata Consultancy Services Limited, Mumbai (IN)

(72) Inventors: Snehasis Banerjee, Kolkata (IN); Swarnava Dey, Kolkata (IN); Arijit Mukherjee, Kolkata (IN); Swagata Biswas, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 294 days.

(21) Appl. No.: 15/901,978

(22) Filed: Feb. 22, 2018

(65) Prior Publication Data

US 2019/0026551 A1    Jan. 24, 2019

(30) Foreign Application Priority Data

Jul. 24, 2017    (IN) .............................. 201721026253

(51) Int. Cl.
*G06K 9/00*    (2006.01)
*G01R 13/02*    (2006.01)
(Continued)

(52) U.S. Cl.
CPC .......... *G06K 9/00503* (2013.01); *G01R 13/02* (2013.01); *G06F 17/148* (2013.01);
(Continued)

(58) Field of Classification Search
CPC ........... G06K 9/00503; G06K 9/00536; G06K 9/00523; G06N 3/0454; G06N 3/08; G06F 17/148; G01R 13/02
See application file for complete search history.

(56) References Cited

U.S. PATENT DOCUMENTS 5,995,868 A * 11/1999 Dorfmeister ....... A61N 1/36135
600/544
6,105,015 A    8/2000 Nguyen et al.
(Continued)

FOREIGN PATENT DOCUMENTS

WO    WO-2015/049113    4/2015

OTHER PUBLICATIONS

Kang et al., A Method of Mother Wavelet Function Learning for DWT-based Analysis using EEG Signals (Year: 2011).*
(Continued)

*Primary Examiner* — Mohammad K Islam
(74) *Attorney, Agent, or Firm* — Finnegan, Henderson, Farabow, Garrett & Dunner LLP

(57) ABSTRACT

Signal analysis is applied in various industries and medical field. In signal analysis, wavelet analysis plays an important role. The wavelet analysis needs to identify a mother wavelet associated with an input signal. However, identifying the mother wavelet associated with the input signal in an automatic way is challenging. Systems and methods of the present disclosure provides signal analysis with automatic selection of wavelets associated with the input signal. The method provided in the present disclosure receives the input signal and a set of parameters associated with the signal. Further, the input signal is analyzed converted into waveform. The waveforms are analyzed to provide image units. Further, the image units are processed by a plurality of deep architectures. The deep architectures provides a set of comparison scores and a matching wavelet family is determined by utilizing the set of comparison scores.

11 Claims, 5 Drawing Sheets

(51) Int. Cl.
  *G06F 17/14* (2006.01)
  *G06N 3/08* (2006.01)
  *G06N 3/04* (2006.01)
(52) U.S. Cl.
  CPC ....... *G06K 9/00536* (2013.01); *G06N 3/0454* (2013.01); *G06N 3/08* (2013.01)

(56) References Cited

U.S. PATENT DOCUMENTS

| | | | | |
|---|---|---|---|---|
| 6,108,609 | A * | 8/2000 | Qian | G06F 17/148 382/207 |
| 7,308,134 | B2 | 12/2007 | Wersing et al. | |
| 7,801,592 | B2 * | 9/2010 | Shan | A61B 5/02405 600/509 |
| 8,446,800 | B2 * | 5/2013 | Abe | G04R 20/10 368/47 |
| 8,781,038 | B2 * | 7/2014 | Mori | H04L 7/042 375/343 |
| 9,946,876 | B2 * | 4/2018 | Wojnowicz | G06F 21/565 |
| 10,238,329 | B2 * | 3/2019 | Bansal | G01V 3/14 |
| 10,542,961 | B2 * | 1/2020 | Barsimantov | A61B 7/00 |
| 10,624,586 | B2 * | 4/2020 | Noguchi | A61B 5/0022 |
| 2003/0031369 | A1 * | 2/2003 | Le Pennec | G06T 9/007 382/232 |
| 2004/0010203 | A1 * | 1/2004 | Bibian | A61B 5/4821 600/544 |
| 2004/0230387 | A1 * | 11/2004 | Bechhoefer | G01R 31/11 702/58 |
| 2005/0119454 | A1 * | 6/2005 | Mandell | C07K 7/083 530/326 |
| 2005/0197590 | A1 * | 9/2005 | Osorio | A61B 5/4094 600/544 |
| 2007/0032737 | A1 * | 2/2007 | Causevic | A61B 5/411 600/544 |
| 2008/0045328 | A1 * | 2/2008 | Itagaki | A63F 13/40 463/23 |
| 2008/0208072 | A1 * | 8/2008 | Fadem | A61B 5/726 600/544 |
| 2008/0208073 | A1 * | 8/2008 | Causevic | A61B 5/048 600/544 |
| 2009/0247893 | A1 * | 10/2009 | Lapinlampi | A61B 5/0488 600/544 |
| 2010/0114813 | A1 * | 5/2010 | Zalay | A61B 5/048 706/58 |
| 2010/0191792 | A1 * | 7/2010 | Brown | G06F 17/148 708/404 |
| 2011/0055222 | A1 * | 3/2011 | Choudur | G06F 17/148 707/748 |
| 2012/0123232 | A1 | 5/2012 | Najarian et al. | |
| 2015/0038869 | A1 * | 2/2015 | Simon | A61B 5/0006 600/544 |
| 2015/0045684 | A1 | 2/2015 | Schie et al. | |
| 2016/0029946 | A1 * | 2/2016 | Simon | A61B 5/048 600/544 |
| 2017/0108456 | A1 * | 4/2017 | Alizadeh | G01M 5/0083 |
| 2017/0311870 | A1 * | 11/2017 | Bardakjian | A61B 5/4094 |
| 2017/0347906 | A1 * | 12/2017 | Intrator | A61B 5/6803 |

OTHER PUBLICATIONS

Safari, P. (Dec. 2013). Deep Learning for Sequential Pattern Recognition (Master's Thesis). Retrieved from https://upcommons.upc.edu/bitstream/handle/2099.1/20268/main.pdf.

Singh, L. et al. "A Comparative Study of MRI Data using Various Machine Learning and Patter Recognition Algorithms to Detect Brain Abnormalities," *Proceedings of the Tenth Australasian Data Mining Conference (AusDM 2012)*, Sydney, Australia, Dec. 5-7, 2012; pp. 157-165.

* cited by examiner

SYSTEM AND METHOD FOR SIGNAL ANALYSIS

PRIORITY CLAIM

This U.S. patent application claims priority under 35 U.S.C. § 119 to: India Application No. 201721026253, filed on Jul. 24, 2017. The entire contents of the aforementioned application are incorporated herein by reference

TECHNICAL FIELD

The embodiments herein generally relates, in general, to signal processing and, in particular, to a system and method for signal analysis.

BACKGROUND

Signal analysis is a key technology used in industry, medical field, astronomy, nuclear engineering, sub-band coding, optics, turbulence, earthquake prediction, etc. In signal analysis, an information associated with a signal is analyzed to identify the functionality of a system or a device. For example, by analyzing a cardiac signal of a patient, cardiac health of a patient can be assessed. However, the information about the signal is distributed across both time and frequency domain. The information distributed across the time domain can be analyzed using time domain analysis. For example, the cardiac signal rate can be different at different time interval. Typically, the frequency domain of a signal can be analyzed using techniques, for example, Fast Fourier Transform (FFT), Discrete Fourier Transform (DFT), etc. However, while analyzing the time domain of the signal, the information about the frequency domain may be lost and while analyzing the frequency domain of the signal, the information about the time domain may be lost.

Conventional methods are able to analyze either the frequency domain of the signal or the time domain of the signal. But, there is a challenge in analyzing both the frequency domain and time domain of a signal simultaneously. Hence wavelet transforms are used for analyzing the time domain and frequency domain of a signal simultaneously. In wavelet transform, a mother wavelet plays an important role in analyzing the signal. The mother wavelet is a prototype function for generating various wavelets with varying scale. But, selecting a mother wavelet is a challenging task because a set of properties of the mother wavelet and a set of properties of the signal to be analyzed should be matched carefully. The conventional methods mostly rely on manual selection of mother wavelets and some of the automated methods may be inefficient in analyzing the signal in an efficient manner.

SUMMARY

Embodiments of the present disclosure present technological improvements as solutions to one or more of the above-mentioned technical problems recognized by the inventors in conventional systems. For example, in one embodiment, a method for signal analysis is provided. The method includes receiving, the one or more signals, wherein the one or more signals are associated with at least one signal parameter and a prior information by the one or more hardware processors. Further, the method includes chopping, each signal of the one or more signals into a plurality of chopped signal units based on an optimized signal chopping window, by the one or more hardware processors. The optimized signal chopping window is determined by utilizing the at least one signal parameter associated with the one or more signals and prior information available for the one or more signals. The at least one parameter associated with each signal and the prior information available for the one or more signals is stored in a database. Furthermore the method includes converting, each chopped signal unit of the plurality of chopped signal units into a waveform, by the one or more hardware processors. Furthermore the method includes comparing, each waveform corresponding to the plurality of chopped signal units with a plurality of waveforms associated with a plurality of known wavelet families to determine an ideal window size for scaling, by the one or more hardware processors. Furthermore the method includes scaling, each waveform corresponding to the plurality of chopped signal units by utilizing the ideal scaling window to obtain one or more scaled waveforms, by the one or more hardware processors. Furthermore, the method includes obtaining, one or more image units by converting every scaled waveform among the one or more scaled waveforms into an image corresponding to the scaled waveform, by the one or more hardware processors. Furthermore the method includes obtaining, one or more mother wavelets and a plurality of variants of the one or more mother wavelets by comparing each image unit among the one or more image units with a plurality of known wavelet families to obtain a set of comparison scores based on a deep architecture mechanism, by the one or more hardware processors. The deep architecture mechanism to obtain a set of comparison scores analyzes each image unit using a plurality of deep architectures simultaneously to obtain the set of comparison scores, wherein each comparison score among the set of comparison scores indicates the percentage of matching of the image unit with the known wavelet families. Furthermore, the method includes determining, a matching wavelet family based on the set of comparison scores, by the one or more hardware processors.

In another aspect, a system for signal analysis is provided. The system includes one or more memories comprising programmed instructions and repository for storing the one or more signals, a signal database, a wavelet database, at least one parameter associated with the one or more signal and a prior information available for the one or more signals; and one or more hardware processors operatively coupled to the one or more memories, wherein the one or more hardware processors are capable of executing the programmed instructions stored in the one or more memories, and a signal analysis unit, wherein the signal analysis unit is configured to receive, the one or more signals, wherein the one or more signals are associated with at least one signal parameter and the prior information. Further the signal analysis unit is configured to chop, each signal of the one or more signals into a plurality of chopped signal units based on an optimized signal chopping window. Furthermore the signal analysis unit is configured to convert, each chopped signal unit of the plurality of chopped signal units into a waveform. Furthermore the signal analysis unit is configured to compare, each waveform corresponding to the plurality of chopped signal units with a plurality of waveforms associated with a plurality of known wavelet families to determine an ideal window size for scaling. Furthermore the signal analysis unit is configured to scale, each waveform corresponding to the plurality of chopped signal units by utilizing the ideal scaling window to obtain one or more scaled waveforms. Furthermore the signal analysis unit is configured to obtain, one or more image units by converting every scaled waveform among the one or more scaled waveforms into an image corresponding to the scaled waveform. Furthermore, the signal analysis unit is configured to obtain, one or more mother wavelets and a plurality of variants of the one or more mother wavelets by comparing each image unit among the one or more image units with a plurality of known wavelet families to obtain a set of comparison scores based on a deep architecture mechanism. Furthermore, the signal analysis unit is configured to determine, a matching wavelet family based on the set of comparison scores;

In yet another aspect, a computer program product comprising a non-transitory computer-readable medium having embodied therein a computer program for system and method for signal analysis, is provided. The computer readable program, when executed on a computing device, causes the computing device to receive, the one or more signals, wherein the one or more signals are associated with at least one signal parameter and a prior information. Further, computer readable program, when executed on a computing device, causes the computing device to chop, each signal of the one or more signals into a plurality of chopped signal units based on an optimized signal chopping window. Furthermore, computer readable program, when executed on a computing device, causes the computing device to convert, each chopped signal unit of the plurality of chopped signal units into a waveform. Further, computer readable program, when executed on a computing device, causes the computing device to compare, each waveform corresponding to the plurality of chopped signal units with a plurality of waveforms associated with a plurality of known wavelet families to determine an ideal window size for scaling. Further, computer readable program, when executed on a computing device, causes the computing device to scale, each waveform corresponding to the plurality of chopped signal units by utilizing the ideal scaling window to obtain one or more scaled waveforms. Further, computer readable program, when executed on a computing device, causes the computing device to obtain, one or more image units by converting every scaled waveform among the one or more scaled waveforms into an image corresponding to the scaled waveform. Further, computer readable program, when executed on a computing device, causes the computing device to obtain, one or more mother wavelets and a plurality of variants of the one or more mother wavelets by comparing each image unit among the one or more image units with a plurality of known wavelet families to obtain a set of comparison scores based on a deep architecture mechanism. Further, computer readable program, when executed on a computing device, causes the computing device to determine, a matching wavelet family based on the set of comparison scores.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

Figure 1:
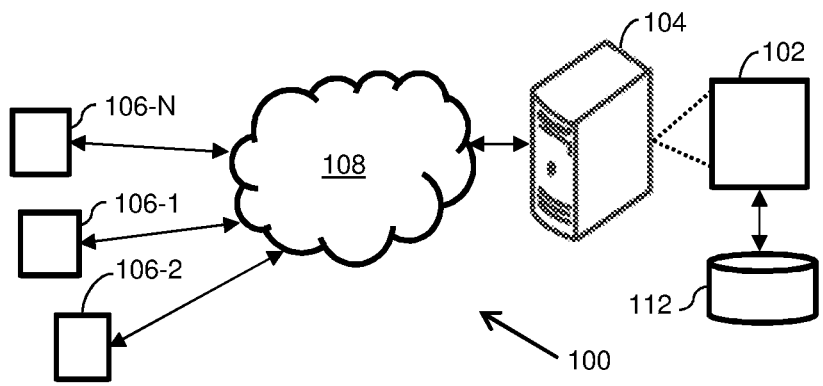
FIG. 1 illustrates a network environment implementing a system and method for signal analysis, according to some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

In the field of signal processing, wavelet analysis plays a vital role to perform signal analysis. The wavelet analysis is generally used for analyzing a signal in both time domain and frequency domain to find out one or more individual components of the signal to take certain decisions. For example, in analyzing cardiac health of a user, a cardiac signal of the user is analyzed with respect to the cardiac signal of a normal user. The variation in rate of the cardiac signal can be used for identifying a cardiac disease associated with the user. In wavelet analysis, a mother wavelet plays an important role because the mother wavelets can be scaled and time shifted to generate a set of child wavelets for further analysis. But, selecting an optimal mother wavelet associated with a set of known wavelet families in an automatic manner is challenging. Some of the known wavelet families including Haar, Daubechies, Symlets, Coiflets, BiorSplines, ReverseBiorthogonal, Meyer, Dmeyer, Gaussian, Mexican_hat, Morlet, Complex Gaussian, Shannon, Frequency B-Spline, Complex Morlet etc.

The present subject matter overcomes the limitations of the conventional signal analysis methods by receiving the signal as input and analyzing the signal to identify the mother wavelet from the known wavelet families in an automatic manner thereby skipping feature engineering used in the conventional methods. Moreover, the present disclosure uses an optimized window size to perform signal analysis using wavelet transform. Additionally, the present disclosure selects an optimized mother wavelet and a set of variants of the mother wavelets in an automatic manner by utilizing a plurality of deep architectures. The plurality of deep architectures are initially trained using a set of datasets. Further, the plurality of deep architectures learns while processing and updates a learning weight. An implementation of the system and method for signal analysis is described further in detail with reference to FIGS. 1 through 6.

Referring now to the drawings, and more particularly to FIG. 1 through 6, where similar reference characters denote corresponding features consistently throughout the figures, there are shown preferred embodiments and these embodiments are described in the context of the following exemplary system and/or method.

FIG. 1 illustrates a network environment 100 implementing a system 102 for signal analysis, according to an example embodiment of the present subject matter. The system for signal analysis 102, hereinafter referred to as the system 102, is configured for signal analysis using one or more known wavelet transforms and the plurality of deep architectures. The one or more known wavelet transforms includes Continuous wavelet transform (CWT), Discrete wavelet transform (DWT), Fast wavelet transform (FWT), Lifting scheme and Generalized Lifting Scheme, Wavelet packet decomposition (WPD), Stationary wavelet transform (SWT), Fractional Fourier transform (FRFT), Fractional wavelet transform (FRWT) etc. The system 102 may be embodied in a computing device, for instance a computing device 104.

Although the present disclosure is explained considering that the system 102 is implemented on a server, it may be understood that the system 102 may also be implemented in a variety of computing systems, such as a laptop computer, a desktop computer, a notebook, a workstation, a cloud-based computing environment and the like. In one implementation, the system 102 may be implemented in a cloud-based environment. It will be understood that the system 102 may be accessed by multiple users through one or more user devices 106-1, 106-2 . . . 106-N, collectively referred to as user devices 106 hereinafter, or applications residing on the user devices 106. Examples of the user devices 106 may include, but are not limited to, a portable computer, a personal digital assistant, a handheld device, a Smartphone, a Tablet Computer, a workstation and the like. The user devices 106 are communicatively coupled to the system 102 through a network 108.

In an embodiment, the network 108 may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 108 may include a variety of network devices, including routers, bridges, servers, computing devices, storage devices. The network devices within the network 108 may interact with the system 102 through communication links.

As discussed above, the system 102 may be implemented in a computing device 104, such as a hand-held device, a laptop or other portable computer, a tablet computer, a mobile phone, a PDA, a smartphone, and a desktop computer. The system 102 may also be implemented in a workstation, a mainframe computer, a server, and a network server. In an embodiment, the system 102 may be coupled to a data repository, for example, a repository 112. The repository 112 may store data processed, received, and generated by the system 102. In an alternate embodiment, the system 102 may include the data repository 112. The components and functionalities of the system 102 are described further in detail with reference to FIG. 2.

Figure 2:
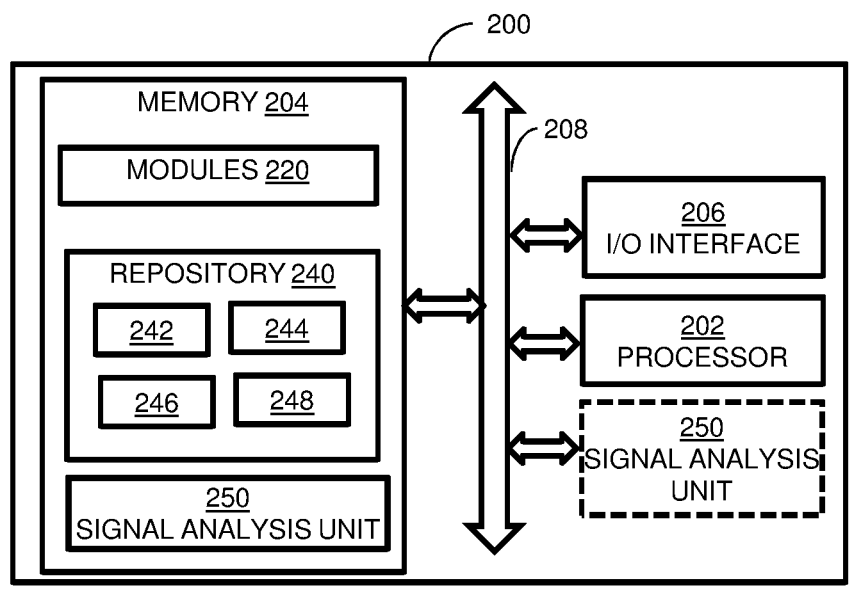
FIG. 2 illustrates a block diagram of a system and method for signal analysis, according to some embodiments of the present disclosure.

FIG. 2 illustrates a block diagram of the signal analysis system 200 for analyzing the signals, according to some embodiments of the present disclosure. The signal analysis system 200 (hereinafter referred to as system 200) may be an example of the system 102 (FIG. 1). In an example embodiment, the system 200 may be embodied in, or is in direct communication with the system, for example the system 102 (FIG. 1). The system 200 includes or is otherwise in communication with one or more hardware processors such as a processor 202, at least one memory such as a memory 204, an I/O interface 206 and a signal analysis unit 250. In an embodiment, the signal analysis unit 250 can be implemented as a standalone unit in the system 200 comprising an input signal receiving module (not shown in FIG. 2), a signal analyzer module (not shown in FIG. 2), a wavelet analyzer module (not shown in FIG. 2), a deep architecture module (not shown in FIG. 2), a score vote module (not shown in FIG. 2) and a comparison module (not shown in FIG. 2). In another embodiment, the signal analysis unit 250 can be implemented as a module in the memory 204 comprising the input signal receiving module (not shown in FIG. 2), the signal analyzer module (not shown in FIG. 2), the wavelet analyzer module (not shown in FIG. 2), the deep architecture module (not shown in FIG. 2), the score vote module (not shown in FIG. 2) and the comparison module (not shown in FIG. 2). The processor 202, memory 204, and the I/O interface 206 may be coupled by a system bus such as a system bus 208 or a similar mechanism.

The I/O interface 206 may include a variety of software and hardware interfaces, for example, a web interface, a graphical user interface, and the like. The interfaces 206 may include a variety of software and hardware interfaces, for example, interfaces for peripheral device(s), such as a keyboard, a mouse, an external memory, a camera device, and a printer. Further, the interfaces 206 may enable the system 102 to communicate with other devices, such as web servers and external databases. The interfaces 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 206 may include one or more ports for connecting a number of computing systems with one another or to another server computer. The I/O interface 206 may include one or more ports for connecting a number of devices to one another or to another server.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220 and the signal analysis unit 250. The modules 220 may include routines, programs, objects, components, data structures, and so on, which perform particular tasks or implement particular abstract data types.

The memory 204 also includes module(s) 220 and a data repository 240. The module(s) 220 include programs or coded instructions that supplement applications or functions performed by the signal analysis system 200. The modules 220, amongst other things, can include routines, programs, objects, components, and data structures, which perform particular tasks or implement particular abstract data types. The modules 220 may also be used as, signal processor(s), state machine(s), logic circuitries, and/or any other device or component that manipulates signals based on operational instructions. Further, the modules 220 can be used by hardware, by computer-readable instructions executed by a processing unit, or by a combination thereof. The modules 220 can include various sub-modules (not shown). The module 220 may include computer-readable instructions that supplement applications or functions performed by the signal analysis system 200.

The data repository 240 may include received input signals 242, a signal database 244, a wavelet database 246 and other data 248. Further, the other data 248 amongst other things, may serve as a repository for storing data that is processed, received, or generated as a result of the execution of one or more modules in the module(s) 220 and the modules associated with the signal analysis unit 250. The repository 240 is further configured to maintain a plurality of parameters and prior information associated with a signal stored in the data repository 240.

Although the data repository 240 is shown internal to the signal analysis system 200, it will be noted that, in alternate embodiments, the data repository 240 can also be implemented external to the signal analysis system 200, where the data repository 240 may be stored within a database (not shown in FIG. 2) communicatively coupled to the signal analysis system 200. The data contained within such external database may be periodically updated. For example, new data may be added into the database (not shown in FIG. 2) and/or existing data may be modified and/or non-useful data may be deleted from the database (not shown in FIG. 2). In one example, the data may be stored in an external system, such as a Lightweight Directory Access Protocol (LDAP) directory and a Relational Database Management System (RDBMS). In another embodiment, the data stored in the data repository 240 may be distributed between the signal analysis system 200 and the external database.

The signal analysis unit 250 of the signal analysis system 200 can be configured to receive, one or more signals, wherein the one or more signals are associated with at least one signal parameter. Herein, the one or more signal refers to an electric current or electromagnetic field used to convey data from one location to another. The one or more signal can be associated with a plurality of parameters and a plurality of prior information. The plurality of parameters associated with the one or more signal including voltage, amplitude, angular frequency, phase angle etc. The plurality of parameters and the plurality of prior information associated with the one or more signal are stored in a signal database and a wavelet database. In an embodiment, the prior information about the one or more signals can include an information related to a signal. The method of creating the signal database and wavelet database is further explained with reference to FIG. 4.

Further, the signal analysis unit 250 of the signal analysis system 200 can be further configured to chop, each signal of the one or more signals into a plurality of chopped signal units based on an optimized signal chopping window. Here, the optimized signal chopping window is obtained by utilizing the at least one signal parameter associated with the one or more signals and the prior information available for the one or more signals. Here, a set of window sizes are applied to the one or more signals for generating a number of signal units. Further, a window size among the set of window sizes generating maximum number of signal units can be selected as the optimized signal chopping window.

Further, the signal analysis unit 250 of the signal analysis system 200 can be configured to convert, each chopped signal unit of the plurality of chopped signal units into a waveform. The signal analysis unit 250 is further configured to compare, each waveform corresponding to the plurality of chopped signal units with a plurality of waveforms associated with a plurality of known wavelet families to determine an ideal window size for scaling. Here, the comparison is performed based on wavelet similarity comparison algorithms, for example energy to entropy ratio algorithm. Further, each waveform corresponding to the plurality of chopped signal units is scaled based on the ideal scaling window to obtain one or more scaled waveforms.

The signal analysis unit 250 of the signal analysis system 200 is further configured to obtain, one or more image units by converting every scaled waveform among the one or more scaled waveforms into an image corresponding to the scaled waveform. Further, one or more mother wavelets and a plurality of variants of the one or more mother wavelets are obtained by comparing each image unit among the one or more image units with a plurality of known wavelet families to obtain a set of comparison scores based on a deep architecture mechanism. Here, the deep architecture mechanism includes a plurality of deep architecture. The deep architecture includes Deep belief networks, Convolutional neural networks, Convolutional Deep Belief Networks, Large Memory Storage and Retrieval (LAMSTAR) neural networks, Deep Boltzmann Machines, Stacked (Denoising) Auto-Encoders, Deep stacking networks, Tensor Deep Stacking Networks (T-DSN), Spike-and-Slab RBMs (SSRBMs), Compound Hierarchical-Deep Models, Deep Coding Networks, Multilayer Kernel Machine, Deep Q-Networks and Memory networks variants. The method of calculation of a comparison score among the set of comparison score by the individual deep architecture is explained with reference to FIG. 5.

Figure 5:
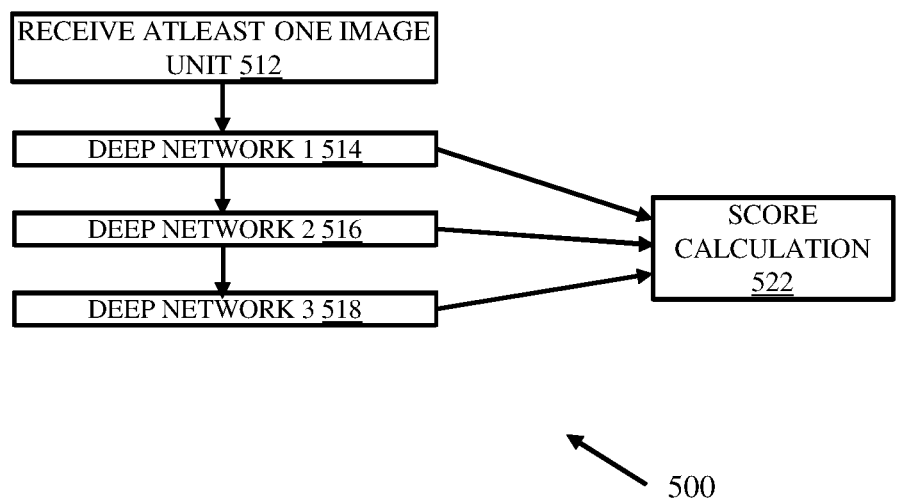
FIG. 5 illustrates a flow diagram for classification of a mother wavelet in an individual deep architecture of FIG. 3, according to some embodiments of the present disclosure.

Now, referring to FIG. 5, a flow diagram for classification of a mother wavelet in an individual deep architecture, according to some embodiments of the present disclosure is described. At step 512, the image unit is received from the wavelet analyzer 306. At step 514, the image unit is analyzed by a deep network1 and scores are obtained. The scores are: 1) optimal window sizes and 2) bias towards identifying a particular set of known wavelet family. At step 516, a set of mother wavelets are obtained corresponding to the bias associated with a wavelet family by a deep network2. The set of mother wavelets are with the optimal window size. At step 518, a set of child wavelets of various scales are obtained and the wavelet family equivalent to the received image unit is identified by a deep network3. Here, a window size of the child wavelets can be within the ideal window size of matched mother wavelets. Further, a comparison score is calculated for the identified wavelet family of the image unit at step 522.

The signal analysis unit 250 of the signal analysis system 200 is further configured to determine, a matching wavelet family based on a set of comparison scores associated with the image unit using the plurality of deep architectures. Here, the matching wavelet family is determined by the following steps (i) receiving the set of comparison scores from the plurality of deep architectures pertaining to the image unit (ii) obtaining a majority vote from the plurality of comparison scores pertaining to the image unit by utilizing a majority vote algorithm and (iii) tagging a signal of the one or more signals pertaining to the image unit with the matching wavelet family by utilizing the majority vote. Here, the image unit with majority vote above a predetermined threshold are tagged into a known wavelet family and the signal of one or more signals pertaining to the image unit with majority vote below the predetermined threshold are tagged into an unknown wavelet family.

Figure 3:
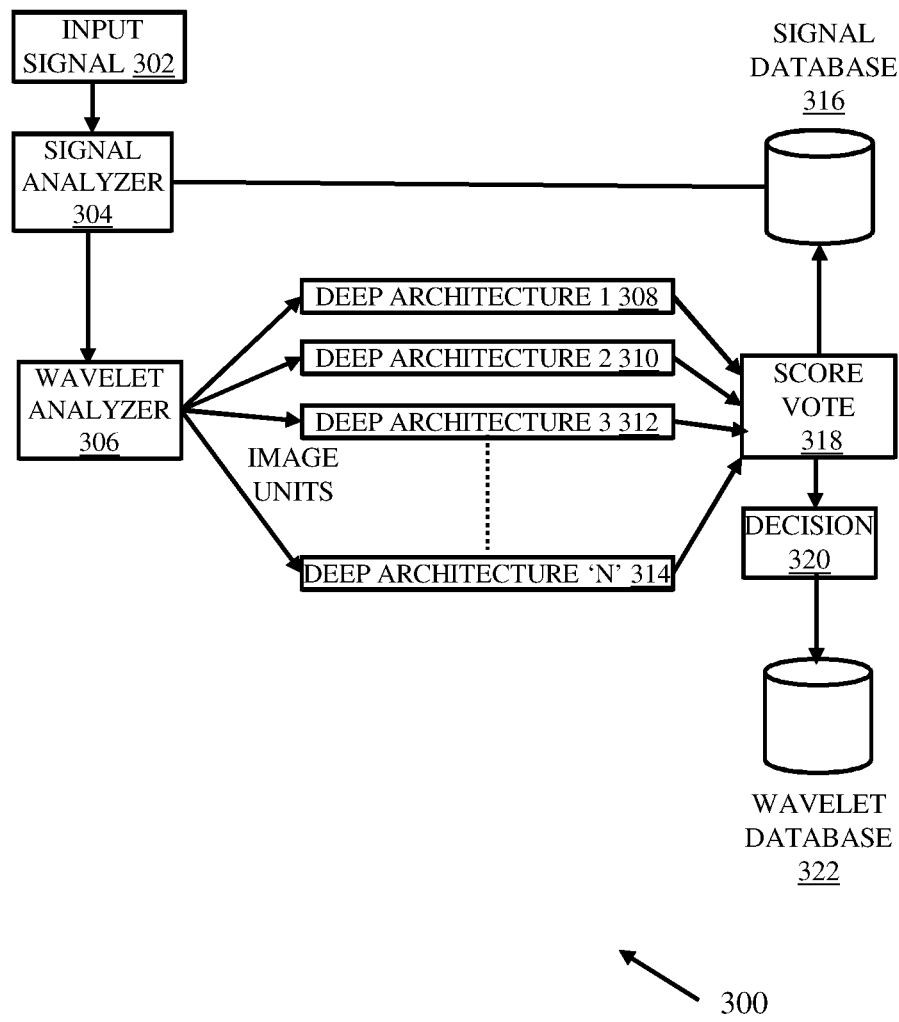
FIG. 3 depicts an architecture diagram for a system and method for signal analysis according to some embodiments of the present disclosure.

FIG. 3 depicts an architecture diagram for a system and method for signal analysis according to some embodiments of the present disclosure. An input signal 302 is received and inputted to a signal analyzer 304. In an embodiment the input signal can be a raw signal. The input signal can be received in at least one of online mode or offline mode. Additionally, the input signal includes at least one signal parameter and prior information associated with the input signal 302. The signal analyzer 304 chops the input signal 302 into a plurality of chopped signal units based on an optimized signal chopping window. The optimized signal chopping window is determined by utilizing the at least one signal parameter associated with the input signal 302. Here, the at least one parameter associated with each signal and prior information about the signal is stored in a signal database 316. The chopped signal units are inputted to a wavelet analyzer 306. The wavelet analyzer 306, converts each chopped signal unit among the plurality of chopped signal units into a waveform. The waveform is compared with one or more waveforms associated with a plurality of known wavelet families to determine an ideal window size for scaling. Further, scaling is performed on each waveform to obtain one or more scaled waveforms. Here, the scaling is performed using the optimized scaling window. Further, the scaled waveforms are converted into corresponding images in an automatic manner to obtain image units. The image units are inputted to 'N' number of deep architectures simultaneously. Every deep architecture calculates a score for the given image unit. For example, for a given image unit, deep architecture1 308 can provide a comparison score on a wavelet family, the given image unit belongs. Similarly, deep architecture2 310 can provide a comparison score on a wavelet family, the given image unit belongs. Similarly 'N' number of deep architecture can provide the corresponding comparison scores for the given image unit. The individual comparison scores calculated by the deep architectures 308, 310, 312 . . . 314 are given as input to a score voting 318. The score vote 318 identifies the majority voting for the given image unit. If the majority voting is higher than a pre-determined threshold, the decision module 320 determines the wavelet family of the given image unit and updates the signal database 316 and the wavelet database 322. If the majority voting is lower than a pre-determined threshold, the decision module 320 sends image unit for human decision to identify a new wavelet family. For example, for the given image unit, the comparison score from deep architecture1 308 is 10 for the Coiflets wavelet family, the comparison score from deep architecture2 310 is 8 for the Symlets wavelet family and the comparison score from deep architecture3 312 is 10 for the Coiflets wavelet family, then the majority voting is for Coiflets Wavelet family. The voting indicates that, the given image unit belongs to the Coiflets wavelet family and hence the signal to which the image unit belongs to is from Coiflets wavelet family. Further, the wavelet family is tagged with the given image unit in the wavelet database 322 and the wavelet family is tagged for the signal in the signal database 316.

The wavelet database 322 and the signal database 316 are trained using large data sets. In an embodiment, a user can search the World Wide Web (WWW) and tag the signal with a corresponding mother wavelet category. Here, a sample representation of the signal and its associated data set stored in the database is represented as follows:

<Signal Dataset 1> <Mother Wavelet 2> <Mother Wavelet 8>
<Signal Dataset 2> <Mother Wavelet 5>
................................................................
................................................................
<Signal Dataset 'n'> <Mother Wavelet 'n'>

Figure 4:
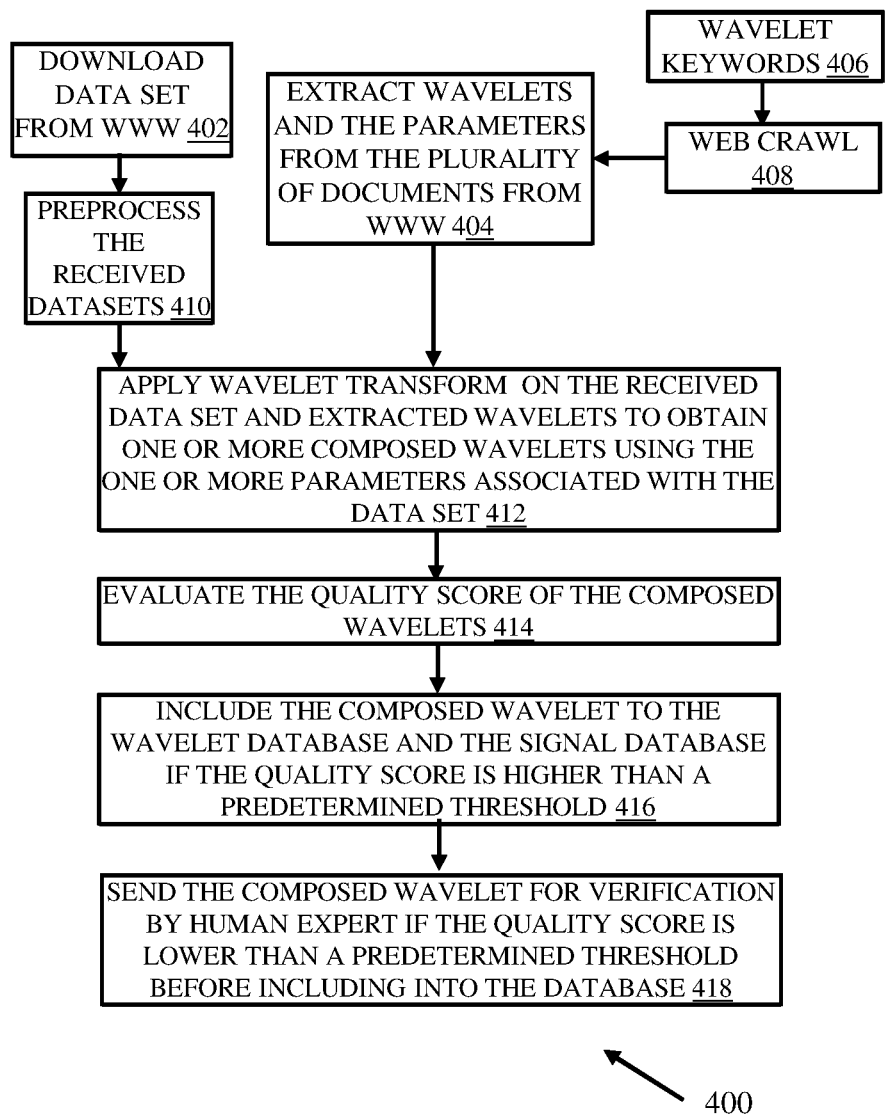
FIG. 4 illustrates a flow diagram for creating a wavelet database and a signal database, according to some embodiments of the present disclosure.

In another embodiment, wavelet database 322 and the signal database 316 can be constructed in an automatic manner. FIG. 4 illustrates a flow diagram for creating the wavelet database 322 and the signal database 316 with signal datasets, according to some embodiments of the present disclosure. In one embodiment, a plurality of data sets available on the WWW can be downloaded at step 402 to obtain a set of downloaded datasets. Further, the downloaded datasets are preprocessed at step 410 to obtain one or more preprocessed datasets. At step 412, Wavelet transform is applied to the one or more preprocessed data sets to obtain one or more composed wavelets using the one or more parameters associated with the extracted wavelets. Here, the one or more parameters associated with the one or more preprocessed data sets are fetched from the signal database 316 and transformed into a set of wavelets in an automatic manner. At step 414, a quality score is calculated for the composed wavelets. At step 416, the composed wavelet is included in the wavelet database 322 based on a pre-determined quality score threshold. For example, if the quality score is higher than the pre-determined quality score threshold, the composed wavelet is included in the database. The quality score threshold is obtained by utilizing a set of information associated with a plurality of performance history associated with the system 200. Further, the composed wavelet with quality score higher than the pre-determined quality score is updated in the signal database 316. At step 418, the composed wavelet is send to human expert for further verification if the quality score is lower than a pre-determined quality score threshold.

In another embodiment, a plurality of documents available in the WWW is searched by utilizing a web crawl 408 by utilizing one or more wavelet keywords 406 for extracting a set of wavelets and the parameters associated with the set of wavelets. The web crawl is a computer program or a software robot to browse the WWW in a methodical and automated manner. The documents include research papers, research articles, other documents and images. At step 412, Wavelet transform is applied on the set of wavelets to obtain one or more composed wavelets using the one or more parameters associated with the set of wavelets. Here, the one or more parameters associated with the set of wavelets are fetched from the wavelet database 322 and transformed into a set wavelets in an automatic manner. At step 414, a quality score is calculated for the composed wavelets. At step 416, the composed wavelet is included in the wavelet database 322 based on a pre-determined quality score threshold. For example, if the quality score is higher than the pre-determined quality score threshold, the composed wavelet is included in the database. The quality score threshold is obtained by utilizing a set of information associated with a plurality of performance history associated with the system 200. Further, the composed wavelet with quality score higher than the pre-determined quality score is updated in the signal database 316. At step 418, the composed wavelet is send to human expert for further verification, if the quality score is lower than a pre-determined quality score threshold.

Figure 6:
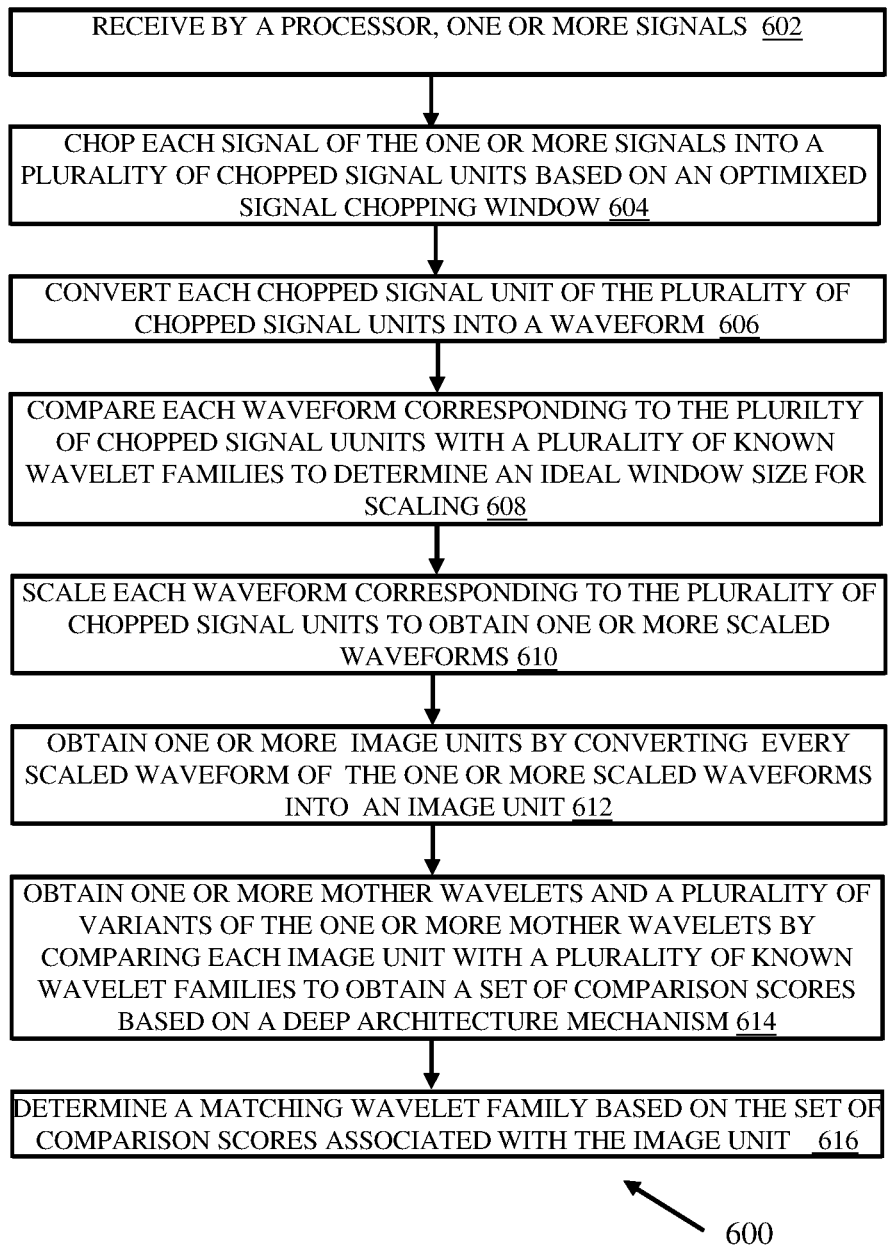
FIG. 6 illustrates a detailed flow diagram for signal analysis, according to some embodiments of the present disclosure.

FIG. 6 illustrates a detailed flow diagram of a method 600 for signal analysis, according to some embodiments of the present disclosure. The method 600 may be described in the general context of computer executable instructions. Generally, computer executable instructions can include routines, programs, objects, components, data structures, procedures, modules, functions, etc., that perform particular functions or implement particular abstract data types. The method 600 may also be practiced in a distributed computing environment where functions are performed by remote processing devices that are linked through a communication network. The order in which the method 600 is described is not intended to be construed as a limitation, and any number of the described method blocks can be combined in any order to implement the method 600, or an alternative method. Furthermore, the method 600 can be implemented in any suitable hardware, software, firmware, or combination thereof.

At 602, the system 200 receives, by the one or more hardware processors, the one or more signals, wherein the one or more signals are associated with at least one signal parameter. At 604, the system 200 chops, by the one or more hardware processors, each signal of the one or more signals into a plurality of chopped signal units based on an optimized signal chopping window. The optimized signal chopping window is determined by utilizing the at least one signal parameter associated with the one or more signals and prior information available for the one or more signals. The at least one parameter associated with each signal and the prior information available for the one or more signals is stored in a repository. At 606, the system 200 converts, by the one or more hardware processors, each chopped signal unit of the plurality of chopped signal units into a waveform for a comparison. At 608, the system 200 compares, by the one or more hardware processors, each waveform corresponding to the plurality of chopped signal units with a plurality of waveforms associated with a plurality of known wavelet families to determine an ideal window size for scaling. At 610, the system 200 scales, by the one or more hardware processors, each waveform corresponding to the plurality of chopped signal units by utilizing the ideal scaling window to obtain one or more scaled waveforms. At 612, the system 200 obtains, by the one or more hardware processors, one or more image units by converting every scaled waveform among the one or more scaled waveforms into an image corresponding to the scaled waveform. At 614, the system 200 obtains, by the one or more hardware processors, one or more mother wavelets and a plurality of variants of the one or more mother wavelets by comparing each image unit among the one or more image units with a plurality of known wavelet families to obtain a set of comparison scores based on a deep architecture mechanism. The deep architecture mechanism to obtain a set of comparison scores analyzes each image unit using a plurality of deep architectures simultaneously to obtain the set of comparison scores, wherein each comparison score among the set of comparison scores indicates the percentage of matching of the image unit with the known wavelet families. At 616, the system 200 determines, by the one or more hardware processors, a matching wavelet family based on the set of comparison scores. Here, the matching wavelet family is determined by utilizing the following steps: (i) receiving the set of comparison scores from the plurality of deep architectures pertaining to the image unit (ii) obtaining a majority vote from the plurality of comparison scores pertaining to the image unit by utilizing a majority vote algorithm and (iii) tagging a signal of the one or more signals pertaining to the image unit with the matching wavelet family among the plurality of known wavelet families based on the majority vote. Here, the input signal is tagged to a known wavelet family based on a comparison between the majority vote and a predetermined threshold. Further, the input signal is tagged to an unknown wavelet family based on a comparison between the majority vote and the predetermined threshold.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Various embodiments disclose methods and system for signal analysis are able to analyse a signal by identifying a mother wavelet associated with the signal in an automatic manner. Here, the system provides an optimized signal analysis by utilizing a plurality of deep architectures. The utilization of deep architectures improves the efficiency of the system further by eliminating a feature engineering part of the conventional methods for signal analysis. In addition to handling known wavelet transforms the system is capable of handling new wavelet transforms. Further, in the present disclosure the wavelet database and signal database can be created in an automatic manner.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for analysis of one or more signals by implementing in a computing device, the method comprising:
    receiving, by one or more hardware processors, the one or more signals, wherein the one or more signals are associated with at least one signal parameter and a prior information;
    chopping, by the one or more hardware processors, each signal of the one or more signals into a plurality of chopped signal units based on an optimized signal chopping window wherein the optimized signal chopping window is a window with maximum number of signal units;
    converting, by the one or more hardware processors, each chopped signal unit of the plurality of chopped signal units into a waveform;
    comparing, by the one or more hardware processors, each waveform corresponding to the plurality of chopped signal units with a plurality of waveforms associated with a plurality of known wavelet families to determine an ideal window size wherein the ideal window size comparison is performed based on wavelet similarity comparison algorithms;
    scaling, by the one or more hardware processors, each waveform corresponding to the plurality of chopped signal units based on an ideal scaling window to obtain one or more scaled waveforms wherein the ideal scaling window is a scaling window with a size equal to the ideal window;
    obtaining, by the one or more hardware processors, one or more image units by converting each of the one or more scaled waveforms into an image corresponding to the scaled waveform;
    obtaining, by the one or more hardware processors, one or more mother wavelets and a plurality of variants of the one or more mother wavelets by comparing each of the image units among the one or more image units with the plurality of known wavelet families to obtain a set of comparison scores based on a deep architecture mechanism; and
    determining a matching wavelet family based on the set of comparison scores.

2. The processor implemented method of claim 1, wherein the optimized signal chopping window is determined by utilizing the at least one signal parameter associated with the one or more signals and the prior information available for the one or more signals.

3. The processor implemented method of claim 2, wherein the at least one parameter associated with each signal and the prior information available for the one or more signals is stored in a database.

4. The processor implemented method of claim 1, wherein the deep architecture mechanism to obtain a set of comparison scores comprises:
    analyzing each image unit using a plurality of deep architectures simultaneously to obtain the set of comparison scores, wherein each comparison score among the set of comparison scores indicates percentage of matching of the image unit with the plurality of known wavelet families.

5. The processor implemented method of claim 1, wherein determining the matching wavelet family based on the set of comparison scores comprises:
    receiving the set of comparison scores from a plurality of deep architectures pertaining to the image unit;
    obtaining a majority vote from the plurality of comparison scores pertaining to the image unit by utilizing a majority vote algorithm; and
    tagging a signal of the one or more signals pertaining to the image unit with the matching wavelet family among the plurality of known wavelet families based on the majority vote, wherein the signal is tagged to a known wavelet family based on a comparison between the majority vote and a predetermined threshold, wherein the signal is tagged to a unknown wavelet family based on a comparison between the majority vote and the predetermined threshold.

6. A signal analysis system for analysis of one or more signals wherein, the signal analysis system comprising:

one or more memories comprising programmed instructions and a repository for storing the one or more signals, a signal database, a wavelet database, at least one parameter associated with the one or more signal and a prior information available for the one or more signals; and one or more hardware processors operatively coupled to the one or more memories, wherein the one or more hardware processors are capable of executing the programmed instructions stored in the one or more memories, and a signal analysis unit, wherein the signal analysis unit is configured to:

receive, the one or more signals, wherein the one or more signals are associated with the at least one signal parameter and the prior information;

chop, each signal of the one or more signals into a plurality of chopped signal units based on an optimized signal chopping window wherein the optimized signal chopping window is a window with maximum number of signal units;

convert, each chopped signal unit of the plurality of chopped signal units into a waveform for a comparison;

compare, each waveform corresponding to the plurality of chopped signal units with a plurality of waveforms associated with a plurality of known wavelet families to determine an ideal window size for scaling wherein the comparison is performed based on wavelet similarity comparison algorithms;

scale, each waveform corresponding to the plurality of chopped signal units by utilizing an ideal scaling window to obtain one or more scaled waveforms wherein the ideal scaling window is a scaling window with a size equal to the ideal window;

obtain, one or more image units by converting every scaled waveform among the one or more scaled waveforms into an image corresponding to the scaled waveform;

obtain, one or more mother wavelets and a plurality of variants of the one or more mother wavelets by comparing each of the image units among the one or more image units with the plurality of known wavelet families to obtain a set of comparison scores based on a deep architecture mechanism; and determine, a matching wavelet family based on the set of comparison scores.

7. The system of claim 6, wherein the signal analysis unit is configured to:
determine the signal chopping window by utilizing the at least one signal parameter associated with the one or more signals and the prior information available for the one or more signals.

8. The system of claim 6, wherein the signal analysis unit is configured to:
store the at least one parameter associated with each signal and the prior information available for the one or more signals in the repository.

9. The system of claim 6, wherein the signal analysis unit is configured to obtain a set of comparison scores based on a deep architecture mechanism by analyzing each image unit using a plurality of deep architectures simultaneously, wherein each comparison score among the set of comparison scores indicates the percentage of matching of the image unit with the plurality of known wavelet families.

10. The system of claim 6, wherein the signal analysis unit is configured to determine the matching wavelet family based on the set of comparison scores by:
receiving the set of comparison scores from a plurality of deep architectures pertaining to the image unit;
obtaining a majority vote from the plurality of comparison scores pertaining to the image unit by utilizing a majority vote algorithm; and
tagging a signal of the one or more signals pertaining to the image unit with the matching wavelet family among the plurality of known wavelet families based on the majority vote, wherein the signal is tagged to a known wavelet family based on a comparison between the majority vote and a predetermined threshold, wherein the signal is tagged to a unknown wavelet family based on a comparison between the majority vote and the predetermined threshold.

11. One or more non-transitory machine readable information storage mediums comprising one or more instructions which when executed by one or more hardware processors causes:
receiving, by one or more hardware processors, the one or more signals, wherein the one or more signals are associated with at least one signal parameter and a prior information;
chopping, by the one or more hardware processors, each signal of the one or more signals into a plurality of chopped signal units based on an optimized signal chopping window wherein the optimized signal chopping window is a window with maximum number of signal units;
converting, by the one or more hardware processors, each chopped signal unit of the plurality of chopped signal units into a waveform;
comparing, by the one or more hardware processors, each waveform corresponding to the plurality of chopped signal units with a plurality of waveforms associated with a plurality of known wavelet families to determine an ideal window size wherein the comparison is performed based on wavelet similarity comparison algorithms;
scaling, by the one or more hardware processors, each waveform corresponding to the plurality of chopped signal units based on an ideal scaling window to obtain one or more scaled waveforms wherein the ideal scaling window is a scaling window with a size equal to the ideal window;
obtaining, by the one or more hardware processors, one or more image units by converting each of the one or more scaled waveforms into an image corresponding to the scaled waveform;
obtaining, by the one or more hardware processors, one or more mother wavelets and a plurality of variants of the one or more mother wavelets by comparing each of the image units among the one or more image units with the plurality of known wavelet families to obtain a set of comparison scores based on a deep architecture mechanism; and
determining a matching wavelet family based on the set of comparison scores.

* * * * *